(12) United States Patent
Beal et al.

(10) Patent No.: US 11,056,213 B2
(45) Date of Patent: Jul. 6, 2021

(54) IDENTIFYING SIGNATURE SNIPPETS FOR NUCLEIC ACID SEQUENCE TYPES

(71) Applicant: Raytheon BBN Technologies Corp., Cambridge, MA (US)

(72) Inventors: Jacob Stuart Michael Beal, Iowa City, IA (US); Daniel Wyschogrod, Newton, MA (US); Steven Wayne Jilcott, Jr., Foxboro, MA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 691 days.

(21) Appl. No.: 15/371,730

(22) Filed: Dec. 7, 2016

(65) Prior Publication Data

US 2018/0089365 A1 Mar. 29, 2018

Related U.S. Application Data

(60) Provisional application No. 62/399,628, filed on Sep. 26, 2016.

(51) Int. Cl.
| | | |
|---|---|---|
| *G16B 30/00* | (2019.01) | |
| *G16B 50/20* | (2019.01) | |
| *G16B 20/20* | (2019.01) | |
| *G16B 5/20* | (2019.01) | |
| *G16B 40/20* | (2019.01) | |
| *G16B 35/20* | (2019.01) | |

(52) U.S. Cl.
CPC ............... *G16B 30/00* (2019.02); *G16B 5/20* (2019.02); *G16B 20/20* (2019.02); *G16B 35/20* (2019.02); *G16B 40/20* (2019.02); *G16B 50/20* (2019.02)

(58) Field of Classification Search
None
See application file for complete search history.

(56) References Cited

PUBLICATIONS

Fredericks, D. N., and David A. Relman. "Sequence-based identification of microbial pathogens: a reconsideration of Koch's postulates." Clinical microbiology reviews 9.1 (1996): 18-33.*
Melsted, Pall, and Jonathan K. Pritchard. "Efficient counting of k-mers in DNA sequences using a bloom filter." BMC bioinformatics 12.1 (2011): 333.*
Barczak, Amy K., et al. "RNA signatures allow rapid identification of pathogens and antibiotic susceptibilities." Proceedings of the national academy of sciences 109.16 (2012): 6217-6222.*
Wyschogrod et al., "False Alarm Reduction in Automatic Signature Generation for Zero-Day Attacks", Proceedings of the Second Cyberspace Research Workshop, Shreveport, Louisiana, pp. 73-81, 2009.
Wyschogrod et al., "Using Automatic Signature Generation as a Sensor Backend", Proceedings of CSIIRW09, Oak Ridge, TN, 2009.

* cited by examiner

*Primary Examiner* — G Steven Vanni
(74) *Attorney, Agent, or Firm* — Lando & Anastasi, LLP (57) ABSTRACT

A method of identifying regions of malicious organic sequences includes identifying a plurality of benign snippets derived from a first sequence obtained from at least one benign organism; extracting a plurality of candidate signature snippets from a second sequence obtained from a malicious organism; determining, for each of the plurality of candidate signature snippets, whether the candidate signature snippet matches at least one of the plurality of benign snippets; and responsive to the candidate signature snippet not matching the at least one of the plurality of benign snippets, identifying the candidate signature snippet as a malicious signature snippet.

23 Claims, 9 Drawing Sheets

IDENTIFYING SIGNATURE SNIPPETS FOR NUCLEIC ACID SEQUENCE TYPES

CROSS REFERENCE TO RELATED APPLICATIONS

This application claims priority under 35 U.S.C. § 119(e) to U.S. Provisional Application Ser. No. 62/399,628, titled "METHOD FOR IDENTIFICATION OF NUCLEIC ACID SIGNATURES," filed Sep. 26, 2016, which is incorporated herein by reference in its entirety.

BACKGROUND

Technical Field

The application generally relates to detecting malicious genetic sequences, and more particularly, in one aspect, to systems and methods for using sequence filters to identify and/or categorize snippets of malicious genetic sequences.

Background

Laboratories are currently able to manufacture deoxyribonucleic acid (DNA) and other sequences using nucleic acid sequence information. In an example scenario, a customer provides a laboratory with the nucleotides in a genetic sequence—in a format as simple as an electronic text file—and the laboratory synthesizes (i.e., manufactures) the sequence for delivery to the customer. This technology raises the specter of bad actors surreptitiously requesting the synthesis of malicious organisms. Diseases like influenza or anthrax could effectively be "mail ordered", thereby posing a public health risk. To prevent such a scenario, laboratories offering such synthesis services typically examine the genetic sequences provided by customers to ensure that the sequence is not associated with a malicious organism.

Current techniques are capable of recognizing sequences as short as approximately 200 base pairs. Yet recent advances in oligo-based assembly and editing, such as Clustered Regularly Interspaced Short Palindromic Repeat (CRISPR) mechanisms, allow for "clipping and stitching" small segments of DNA together. Unscrupulous customers could therefore avoid being detected by embedding parts of malicious organisms in the DNA sequences of multiple benign organisms, or by otherwise synthesizing malicious organisms in small fragments. The pathogenic sequences from these short or hybrid DNA sequences could then be reassembled into a malicious organism after they are synthesized and delivered.

SUMMARY OF THE INVENTION

Aspects and embodiments are directed to apparatus and methods for identifying "signatures" for nucleic acid sequences (e.g., deoxyribonucleic acid (DNA) sequences, ribonucleic acid (RNA) sequences, amino acid sequences, etc.) of a particular type (e.g., benign or malicious, and/or belonging to a particular genus, species, or sample of organism). A nucleic acid sequence may correspond, e.g., to a gene, pathway, or organism. Techniques disclosed herein are described by way of examples that identify malicious organism "signatures" relatively short snippets of malicious genetic sequences that do not occur in similar but benign organisms. The detection of such a signature in a sequence to be synthesized can therefore indicate, with some level of certainty, that the sequence contains malicious genetic code. Synthesis of the sequence can be rejected or postponed until further investigation and review is completed. Such signatures can also be used to categorize sequences according to the types of organisms (malicious or not) for which the sequence contains genetic information. In general, these examples may be extended to embodiments that identify signatures for various kinds and types of nucleic acid sequences.

To identify signatures of malicious organisms, a sequence of a known malicious organism and sequences for one or more known benign organisms may be used. The respective sequences are broken into relatively short snippets, and malicious organism snippets compared to benign organism snippets. For more efficient comparison, the benign organism snippets may be arranged in a probabilistic data structure, such as a Bloom filter. If a match is found—i.e., the malicious organism snippet is also present in benign organisms—then the malicious organism snippet is not a suitable signature for the malicious organism. On the other hand, if the malicious organism signature snippet is only known to be present in the malicious organism, the malicious organism snippet may be a suitable signature. Suitable signatures may be stored in a malicious signature database along with metadata about the snippet or the corresponding malicious organism, including the organism's species, an identifier of a sample from which the snippet was taken, and/or the location of the snippet within that sample.

In one approach, an unknown sequence (e.g., one provided by a customer) can be tested by comparing it to a signature database that can quickly determine whether the sequence contains one or more signature snippets, thereby identifying the sequence as potentially malicious. Metadata stored with the snippet may be used to facilitate or refine the identification, determine a level of confidence in the identification, or may be provided to other systems or users for further analysis. In a second approach, a sequence to be tested can be compared to multiple such filters, each of which contains signatures for a particular category of organism. For example, one filter may identify influenza signature snippets, and another filter may identify anthrax signature snippets. For more efficient categorization, each filter of signature snippets may be arranged in a probabilistic data structure, such as a Bloom filter. In this manner, a sequence can be categorized according to one or more types of organisms for which it contains genetic information.

The systems and methods described herein are not limited to the identification and/or classification of malicious organisms. For example, in some application, genetic sequences (e.g., from non-malicious organisms) may be compared against a signature database to identify species, taxa, or other category of organism.

According to one aspect, a method of identifying regions of malicious organic sequences is provided. The method includes identifying a plurality of benign snippets derived from a first sequence obtained from at least one benign organism; extracting a plurality of candidate signature snippets from a second sequence obtained from a malicious organism; determining, for each of the plurality of candidate signature snippets, whether the candidate signature snippet matches at least one of the plurality of benign snippets; and responsive to the candidate signature snippet not matching the at least one of the plurality of benign snippets, identifying the candidate signature snippet as a malicious signature snippet.

In one embodiment, the method includes determining if the malicious signature snippet is present in at least one test sequence. In a further embodiment, the method includes determining, for a plurality of malicious signature snippets present in the least one test sequence, a common characteristic of the plurality of malicious signature snippets. In yet a further embodiment, determining the common characteristic of the plurality of malicious signature snippets is performed with reference to metadata about at least one snippet of the plurality of malicious signature snippets. In a further embodiment, the metadata includes at least one of an identifier of a genus of an organism from which the snippet was obtained, an identifier of a species of an organism from which the snippet was obtained, and a location at which the snippet was generated on the second sequence.

In another embodiment, the plurality of benign snippets and the candidate signature snippet are one of DNA snippets, RNA snippets, and amino acid snippets. In another embodiment, the plurality of benign snippets is arranged in a probabilistic data structure. In a further embodiment, the probabilistic data structure is one of a Bloom filter and a search tree.

In one embodiment identifying the plurality of benign snippets comprises extracting the plurality of benign snippets from the first sequence obtained from at least one benign organism. In another embodiment, the at least one benign organism is a non-malicious strain of an organism having at least one malicious strain. In yet another embodiment, the at least one benign organism belongs to a genus having at least one malicious organism.

In another embodiment, the method includes predicting a minimum number of benign snippets to be included in the plurality of benign snippets, the minimum number sufficient to yield a false positive rate below a threshold, the false positive rate being a rate at which candidate signature snippets identified as malicious signature snippets are present in a sequence of a benign organism. In a further embodiment, the minimum number of benign snippets is selected with reference to a malicious organism type.

In one embodiment, the plurality of benign snippets is a plurality of n-length subsequences of the first sequence, and the malicious snippet is an n-length subsequence not in the plurality of n-length subsequences.

In another embodiment, the plurality of candidate signature snippets includes a first plurality of n-length subsequences of the sequence, the first plurality of n-length subsequences each beginning at different positions of the sequence, and the plurality of benign snippets includes a second plurality of n-length subsequences of a known benign sequence, the second plurality of n-length subsequences each beginning at different positions of the known benign sequence. In another embodiment, the malicious snippet is a genetic sequence of a pathogen.

According to another aspect, a system is provided. The system includes a benign snippet database configured to store a plurality of benign snippets from a first sequence obtained from at least one benign organism, and a processor configured to extract a plurality of candidate signature snippets from a second sequence obtained from a malicious organism; determine, for each of the plurality of candidate signature snippets, whether the candidate signature snippet matches at least one of the plurality of benign snippets; and responsive to the candidate signature snippet not matching the at least one of the plurality of benign snippets, identify the candidate signature snippet as a malicious signature snippet.

According to another aspect, a method of classifying biological sequences is provided. The method includes generating a first plurality of sequence snippets from a first plurality of organisms having a first trait; generating a second plurality of sequence snippets from a second plurality of organisms having a second trait; identifying a plurality of benign sequence snippets; and filtering the first plurality of sequence snippets and the second plurality of sequence snippets to remove at least one of the plurality of benign sequence snippets.

According to one embodiment, the method includes determining if a test sequence is present in the first plurality of sequence snippets; responsive to the test sequence being present in the first plurality of sequence snippets, identifying the test sequence as having the first trait; determining if the test sequence is present in the second plurality of sequence snippets; and responsive to the test sequence being present in the second plurality of sequence snippets, identifying the test sequence as having the second trait.

According to another embodiment, the first plurality of sequence snippets, the second plurality of sequence snippets, and the plurality of benign sequence snippets are one of DNA snippets, RNA snippets, and amino acid snippets.

According to yet another embodiment, the first plurality of sequence snippets is arranged in a first probabilistic data structure, and the second plurality of sequence snippets is arranged in a second probabilistic data structure. According to a further embodiment, the first probabilistic data structure and the second probabilistic data structure are each one of a Bloom filter and a search tree.

According to another embodiment, the first trait identifies a first class of pathogens and the second trait identifies a second class of pathogens.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

Systems and methods of identifying and classifying genetic sequences are described. In particular, genetic signatures of malicious organisms (e.g., pathogens like anthrax or influenza) are isolated. Such malicious organism signatures may be snippets of genetic sequences that are present in a malicious organism, but not present in related benign organisms, thereby uniquely identifying the sequence of the malicious organism. Once such malicious organism signatures have been identified, test sequences of unknown makeup can be compared to the malicious organism signatures to quickly determine if the test sequence contains the malicious organism signature. If so, the test sequence may be flagged for further investigation and/or may be identified as containing malicious sequence information.

Different approaches may be used for identifying and/or classifying malicious sequences. According to one approach, a benign snippet database is populated with sequences from known benign organisms. The sequences may represent deoxyribonucleic acid (DNA) sequences, ribonucleic acid (RNA) sequences, amino acid sequences, or the like. The benign snippet database may be arranged as a probabilistic data structure, such as a Bloom filter, and the benign organisms may be selected for their similar structure or classification with malicious organisms of interest.

The system is "trained" by identifying one or more signature snippets for a particular malicious organism. In the training process, a sequence from the malicious organism is broken into candidate signature snippets. The benign snippet database is then examined to determine if each candidate signature snippet is present. If the candidate signature snippet is present in the benign snippet database, the candidate signature snippet is not a suitable signature snippet, i.e., it is not useful in identifying malicious organisms, since it is present in malicious and benign organisms alike. On the other hand, if the candidate signature snippet is not present in the benign snippet database, the candidate snippet may be a malicious signature snippet of use in identifying malicious organisms. That is, the presence of the malicious signature snippet in a test sequence would mean that the test sequence did not originate from any of the benign organisms represented in the benign snippet database. Malicious signature snippets can then be organized in a malicious signature database as part of the training process. Metadata about the snippet and/or the corresponding malicious organism may also be stored, including the organism's species, an identifier of a sample from which the snippet was taken, and the location of the snippet within that sample.

After the training process is complete, the system may test sequences of unknown makeup to determine if they contain any of the malicious signature snippets identified in the training process. A match between a test sequence snippet and a malicious signature snippet in the malicious signature database indicates that the test sequence may contain sequence information for a malicious organism, and the test sequence may be flagged for further review. Metadata stored about a malicious signature snippet matching a region of the test sequence snippet may be referenced to identify or categorize the test sequence or the test sequence snippet. For example, where multiple malicious signature snippets are found in the test sequence, common characteristics of the matching malicious signature snippets may be determined from the metadata. It may be determined, for example, that the matching malicious signature snippets are all from a particular sample (or related samples) of a specific organism, which may suggest that the customer is trying to replicate that organism.

According to another approach, a plurality of signature databases may be employed, with each signature database housing signature snippets for a particular known type or class of organism. For example, an influenza signature database may store signature snippets uniquely present in one or more sequences of influenza organisms, and likewise with an anthrax signature database. In the training process, the snippets in each signature database may be compared to one or more benign snippet databases, as in the approach above, to filter out any snippets present in the benign snippet database, leaving only signature snippets for the organisms represented by the particular signature database.

Test sequences of unknown makeup can then be broken into test sequence snippets and compared to each of the plurality of signature databases. The presence of a test sequence snippet in a particular signature database may indicate that the test sequence snippet contains information for the corresponding organism type. For example, a match of a test sequence snippet with a signature snippet in the influenza signature database may indicate that the test sequence contains some or all of the sequence for an influenza pathogen. Different test sequence snippets from a particular test sequence may match signature snippets in multiple signature databases. The number of matches and/or the location of matches in the test sequence may be used to classify the test sequence, or regions thereof, according to one or more organism types for which it may contain sequence information.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Figure 1:
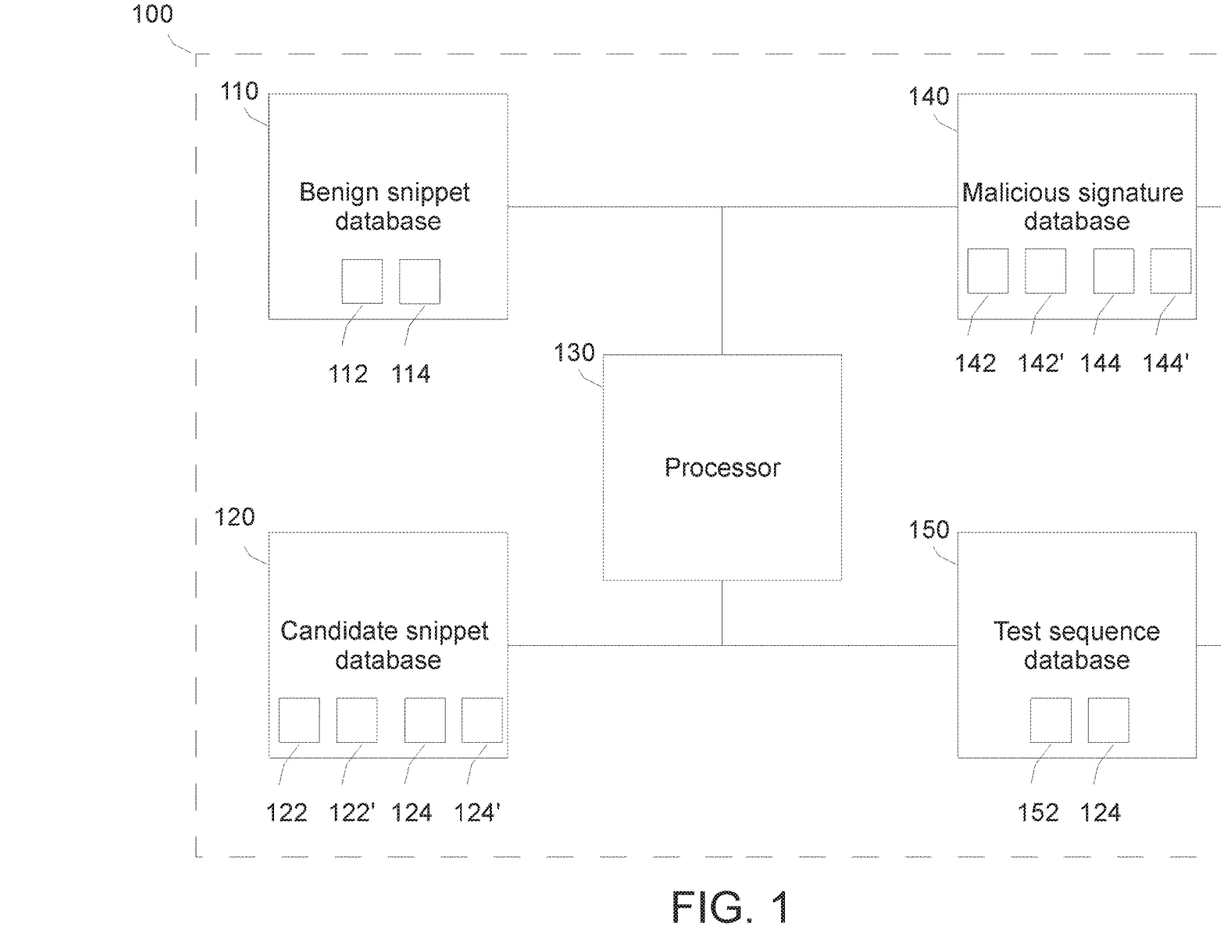
FIG. 1 is a block diagram of a computer system for identifying signature snippets and comparing them to test sequences according to aspects of the invention.

FIG. 1 is a block diagram for a system 100 configured to perform methods of identifying malicious signature snippets. The system 100 includes a benign snippet database 110 configured to store a number of benign snippets 112, 114 derived from benign organism sequences (not shown). The system 100 further includes a candidate signature database 120 configured to store a number of candidate signature snippets 122, 124 derived from malicious organism sequences (not shown), as well as metadata 122', 124' relating to the candidate signature snippets 122, 124.

The system 100 also includes a processor 130 configured to compare each of the candidate signature snippets 122, 124 to the benign snippet database 110 to determine if a given candidate signature snippet 122, 124 matches any of the benign snippets 112, 114. For example, if candidate signature snippet 122 matches benign snippet 112, it is known that the candidate signature snippet 122 does not uniquely identify the malicious organism sequence. On the other hand, if candidate signature snippet 124 does not match either of benign snippets 112, 114, the candidate signature snippet 124 may uniquely identify the malicious organism sequence. In that case, the candidate signature snippet 124 may be stored in the malicious signature database 140 as one of the malicious signature snippets 142, 144, along with metadata 142', 144' relating to the malicious signature snippets 142, 144.

The system 100 further includes a test sequence database 150 configured to store a number of test sequences 152, 154. During a testing operation of the system 100, one or more of the test sequences 152, 154 in the test sequence database 150 is compared to the malicious signature snippets 142, 144 to determine if the malicious signature snippets 142, 144 are present in the one or more of the test sequences 152, 154. If so, any of the test sequences 152, 154 matching any of the malicious signature snippets 142, 144 may be flagged as containing a sequence (or signature snippet thereof) of a malicious organism. In some embodiments, the one or more test sequences 152, 154 may be full genetic sequences (e.g., representing full strands of DNA). In other embodiments, the one or more test sequences 152, 154 may be subsequences of a given length, with an optimal length for testing being selected. In preferred embodiments, the entire one or more test sequence 152, 154 is analyzed, such as in sequential order. In some embodiments, the one or more test sequences 152, 154 may first be compared to the malicious signature snippets 142, 144 at locations on the one or more test sequences 152, 154 where malicious signatures may be expected to be found. If no matches are found, less likely locations may be examined.

In some embodiments, a user interface may be used to display or otherwise provide results of the comparison, and/or to issue an alert or other communication that the test sequence may represent a malicious organism.

The benign snippet database 110 may be structured as a space-efficient probabilistic data structure, such as a Bloom filter. Such filters can be used to quickly and efficiently test whether an element is a member of a set. In the present context, such a filter can be used to quickly determine whether a candidate signature snippet matches one or more benign snippet in the benign snippet database 110 (in which case the candidate signature snippet is definitively not suitable as a malicious signature snippet), or, alternately, whether the candidate signature snippet does not match any benign snippet in the benign snippet database 110 (in which case the candidate signature snippet may be suitable as a malicious signature snippet).

A "false positive" can occur where a candidate signature snippet does not match any benign snippet in the benign snippet database 110, but nonetheless is not unique to a malicious organism sequence—for example, the candidate signature snippet may match a benign snippet that would have been generated from a benign organism sequence on which extraction was not performed. In this situation, a false-positive identification of a malicious signature snippet could cause benign organism sequences to be mistakenly identified as malicious organism sequences during the testing phase of operation, thereby requiring additional (and unnecessary) investigation. To reduce the occurrence of false positives to an acceptable level, a sufficiently large number of benign snippets may be populated in the benign snippet database 110; as the size of the benign snippet database 110 grows, the rate of false-positives approaches zero. In one example for a given organism type, generating benign snippets from a collection of 1.5 million base pairs of benign sequences may yield a false-positive rate of 4%. Increasing the population of base pairs by a factor of ten (to 11.5 million) may reduce the false-positive rate to 0.25%.

In some embodiments, the benign snippet database 110 may be prepopulated with the benign snippets 112, 114 (e.g., from an external source) such that extraction by the system 100 of the benign snippets 112, 114 from benign organism sequences is not necessary. In other embodiments, the benign snippet database 110 and/or the processor 130 may be configured to extract the benign snippets 112, 114 from sequences obtained from one or more known benign organisms. The length n of snippets may be configurable, and snippets of a given length n are referred to herein as n-grams. While the examples shown here use 3-gram snippets, any feasible length n may be used.

Figure 2A:
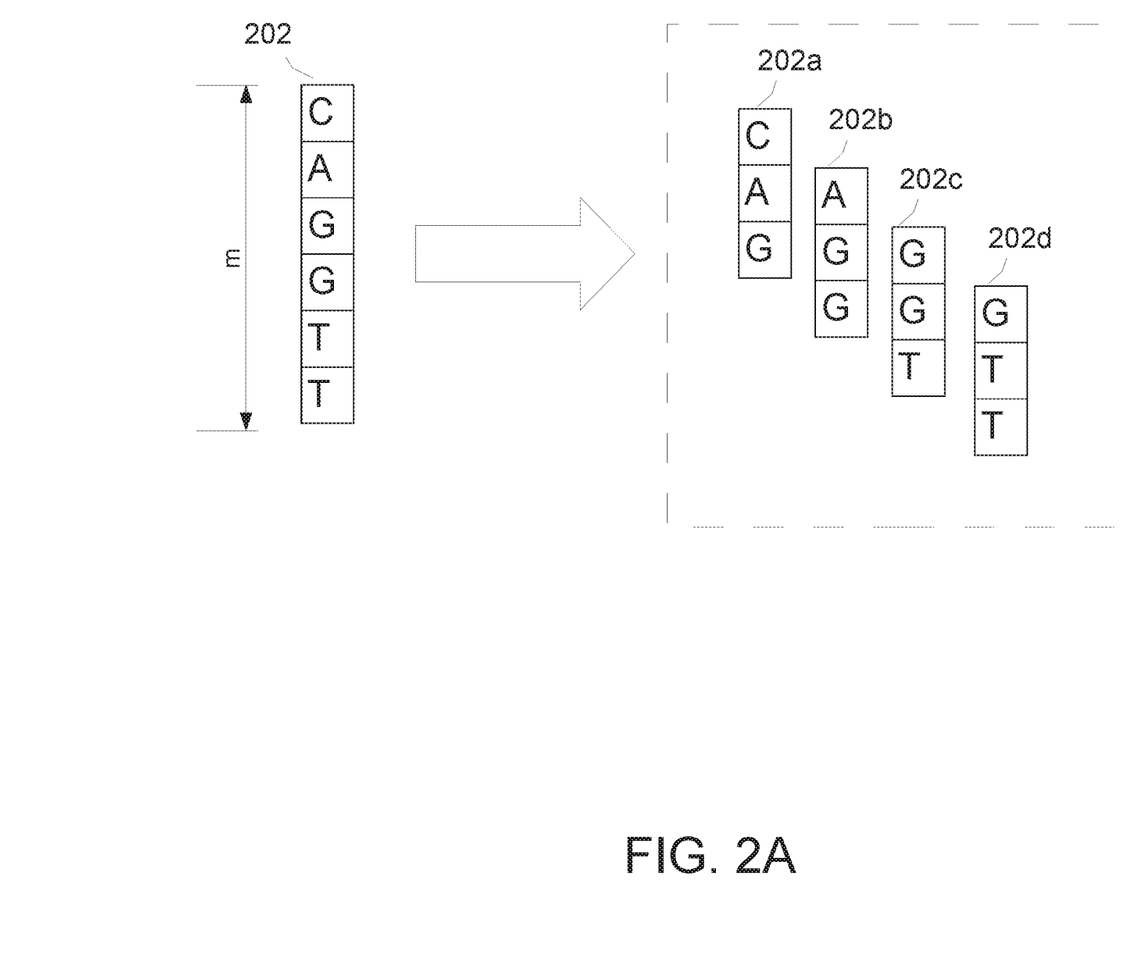
FIG. 2A illustrates the extraction of benign snippets according to aspects of the invention.

FIG. 2A shows how an exemplary benign DNA sequence 202 ("CAGGTT") from a benign organism and including six nucleotides can be extracted into multiple 3-gram snippets 202a-d for storage in the benign snippet database 110 according to some embodiments. Each of the 3-gram snippets 202a-d represents a subsequence of the nucleotides of benign DNA sequence 202 at a different starting point. For example, the first 3-gram snippet 202a contains the 3-nucleotide subsequence ("CAG") starting at the first position of the benign DNA sequence 202, the second 3-gram snippet 202b contains the 3-nucleotide subsequence ("AGG") starting at the second position of the sequence 202, and so forth. A DNA sequence of length m may therefore yield m-n snippets.

Returning to FIG. 1, the candidate signature database 120 and/or the processor 130 may be configured to derive the candidate signature snippets 212, 214 from sequences obtained from one or more known malicious organisms to be detected during the testing phase of operation of the system 100. The length of the candidate signature snippets 212, 214 may be selected to be the same as the n-gram benign snippets (e.g., 3).

Figure 2B:
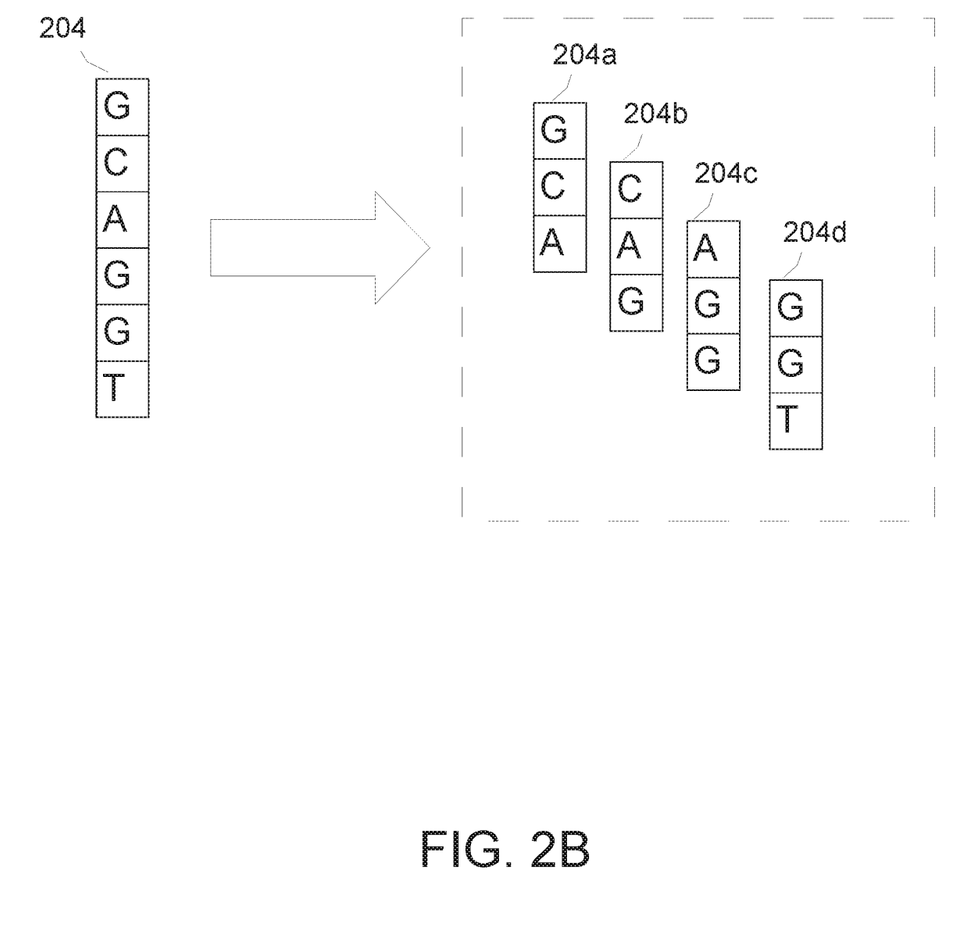
FIG. 2B illustrates the extraction of candidate signature snippets according to aspects of the invention.

FIG. 2B shows how a malicious DNA sequence 204 can be extracted into multiple 3-gram snippets 204a-d for storage in the candidate signature database 120 according to some embodiments. The extraction is performed in much the same way as with the benign DNA sequence 202 in FIG. 2A. For example, the first 3-gram snippet 204a contains the 3-nucleotide subsequence ("GCA") starting at the first position of the malicious DNA sequence 202, the second 3-gram snippet 204b contains the 3-nucleotide subsequence ("CAG") starting at the second position of the sequence 204, and so forth.

The processor 130 is further configured to identify those candidate signature snippets 122, 124 in the candidate signature database 120 that do not match any of the benign snippets 112, 114 in the benign snippet database 110. Candidate signature snippets 122, 124 without such a match can be identified as malicious signature snippets 142, 144 and stored in the malicious signature database 140. Referring to FIGS. 2A and 2B, for example, candidate signature snippet 204b ("CAG") matches benign snippet 202a, candidate signature snippet 204c ("AGG") matches benign snippet 202b, and candidate signature snippet 204d ("GGT") matches benign snippet 202c. Thus, none of candidate signature snippets 204b, 204c, or 204d would be identified as malicious signature snippets. Candidate signature snippet 204a ("GCA") has no match in the benign snippet database 110, however, and would be identified as a malicious signature snippet.

Returning to FIG. 1, any malicious signature snippets 142,144 identified by the processor 130 are stored in the malicious signature database 140.

Each of the benign snippet database 110, the candidate signature database 120, and/or the malicious signature database 140 may be arranged, populated, or optimized to improve performance. For example, duplicate snippets in a given database may be removed, and the snippets stored therein may be sorted or filtered for optimization purposes. In some embodiments, the benign snippet database 110, the candidate signature database 120, and/or the malicious signature database 140 may be stored in an encrypted format, or otherwise secured against access by unauthorized parties, and decrypted at or shortly before runtime.

The candidate signature database 120 and/or the malicious signature database 140 may also store metadata 122', 124', 142', 144' about the snippets they respectively store, or about the corresponding malicious organism. Such metadata may include, for example, a data/time at which the snippet was created; an identifier of the sample/organism from which the snippet was obtained; the location of the snippet in that sample; a unique identifier of the snippet; a species or genus of the corresponding organism; a general category of the organism (e.g., virus, bacteria); or the like.

Figure 3:
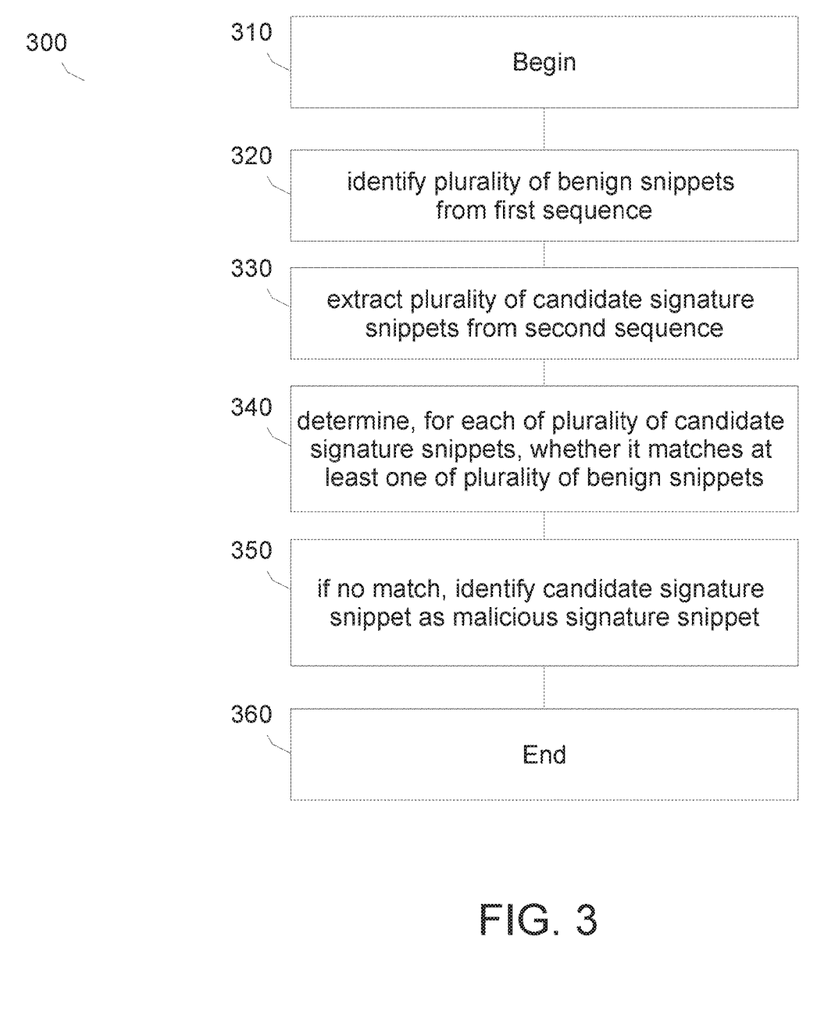
FIG. 3 is a flow diagram of one example of a process of identifying signature snippets according to aspects of the invention.

FIG. 3 is a flow diagram for one example of a method 300 for identifying regions of malicious genetic sequences.

Method 300 begins at step 310.

At step 320, a plurality of benign snippets is identified, the plurality of benign snippets derived from a first sequence obtained from at least one benign organism. In some embodiments, the plurality of benign snippets is extracted from sequences from one or more known benign organisms, as discussed above with reference to FIG. 2A. In particular, benign snippets of length n may be extracted from such benign sequences. The length n of such snippets may be selected to be sufficient to facilitate the identification of malicious signature snippets in later steps. For example, consider a scenario in which a snippet of length n=20 is necessary to uniquely identify a malicious sequence—in other words, there would be no snippets of length n<20 that would be present in a malicious sequence but not present in a benign sequence. In such a scenario, the length n of both the benign snippets and the malicious signature snippets may be 20 (or higher).

As discussed above with reference to FIG. 2A, benign snippets may be extracted from benign sequences by creating, where possible, an n-length snippet corresponding to a subsequence starting at each position in the benign sequence. In other words, each position (e.g., nucleotide) in the benign sequence, and the n subsequent positions (if available), may be represented by a benign snippet. In other embodiments, only certain positions in the benign sequence may be used as the basis for benign snippets. For example, the chemistry of the sequence or other parameters may make it impossible or unlikely for a malicious signature snippet to correspond to particular starting positions on the benign sequence, in which case those particular starting positions may not be used as the basis for extracting benign snippets.

In some embodiments, extraction of benign snippets from the one or more benign sequences may not be performed by the system. Rather, benign snippets may be provided to the system, for example, by a third party, with the extraction already performed. For example, a database of benign snippets may be made available. In another example, the benign snippets may have been extracted by the system during previous operations and maintained, and as such do not need to be extracted again. It will be appreciated that the extraction and/or use of benign snippets to train the system may be performed in a rolling manner, i.e., new benign snippets may be added over time to improve the accuracy of the results.

The plurality of benign snippets may be derived, in whole or in part, from at least one benign organism having at least one characteristic relevant or useful to identifying malicious signature snippets. In some embodiments, benign organisms that are similar in some manner to a malicious organism of interest may be used to extract benign snippets. The similarities between the benign organisms and the malicious organism may reflect similarities in their genetic sequences, allowing the system to identify the relative few differences as malicious signature snippets. For example, the benign organism may be a non-malicious strain of the malicious organism of interest. In another example, the benign organism and the malicious organism may belong to a common genus, or to a broader range of related organisms.

At step 330, a plurality of candidate signature snippets is extracted from a second sequence obtained from a malicious organism. In some embodiments, the extraction is performed as discussed above with reference to FIG. 2B. In particular, In particular, candidate signature snippets of length n may be extracted from sequences obtained from one or more malicious organisms. The length n of such snippets may be selected to be sufficient to facilitate the identification of malicious signature snippets in later steps.

At step 340, it is determined, for each of the plurality of candidate signature snippets, whether the candidate signature snippet matches at least one of the plurality of benign snippets. In some embodiments, the plurality of benign snippets are arranged in the benign snippet database as a probabilistic data structure (e.g., a Bloom filter), and queries are made on the Bloom filter for each candidate signature snippet. In other embodiments, the plurality of benign snippets is organized in an array, a search tree, a relational database, a schema-free database, a collection of n-tuples, or otherwise stored and appropriately queried. In some embodiments, the plurality of benign snippets is de-duplicated, sorted, and/or filtered to increase efficiency.

At step 350, the candidate signature snippet is identified as a malicious signature snippet responsive to the candidate signature snippet not matching the at least one of the plurality of benign sequence snippets. In some embodiments, the candidate signature snippets identified as malicious signature snippets may be stored as malicious signature snippets in the malicious signature database, along with any metadata for the malicious signature snippets. In other embodiments, a separate malicious signature database may not be employed, and the candidate signature snippet may be flagged as a malicious signature snippet in the candidate signature database; at the end of the training process, those candidate signature snippets not flagged as malicious signature snippets may be discarded or otherwise not used during the testing process.

Process 300 ends at step 360.

Once the training process is complete, test sequences may be examined to determine if one or more malicious signature snippets are present; if so, the test sequence may be flagged for further review and/or considered for rejection from a synthesizing/replicating process.

Figure 4:
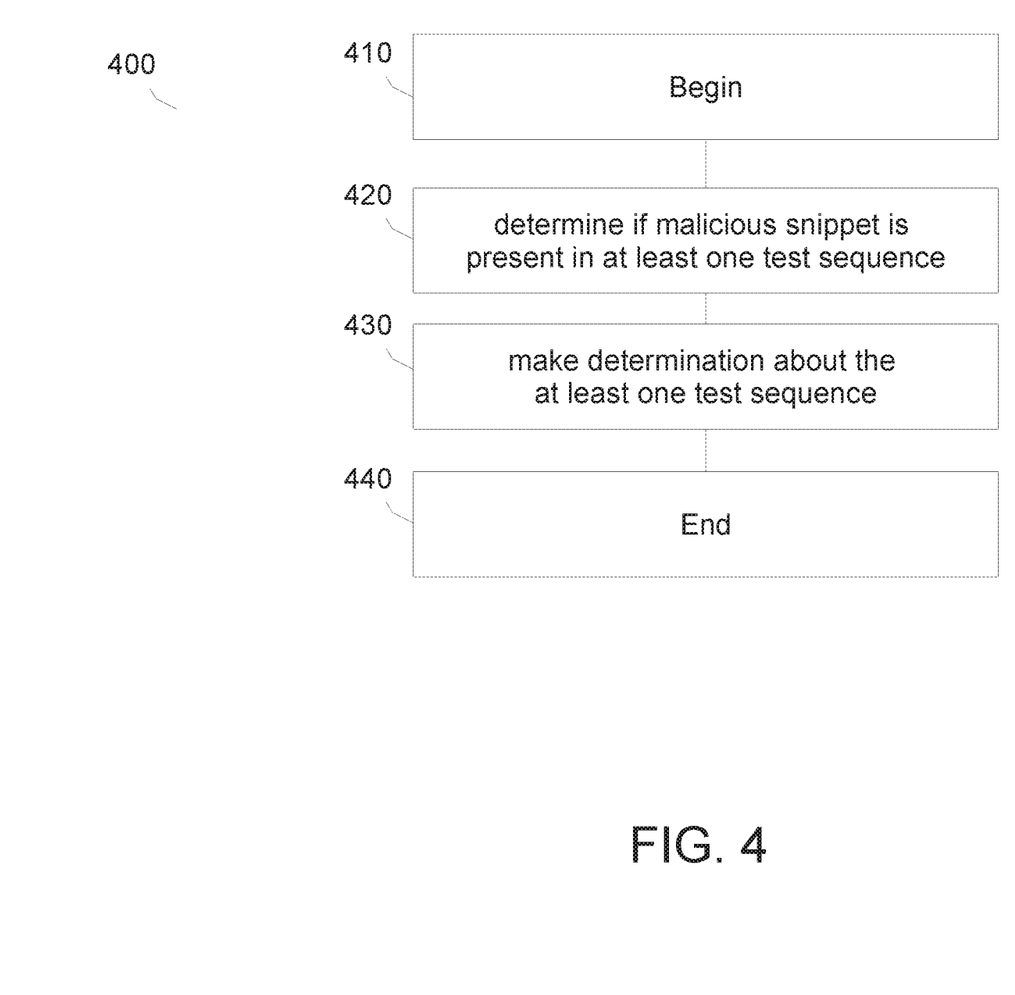
FIG. 4 is a flow diagram of one example of a process of testing test sequences according to aspects of the invention.

FIG. 4 is a flow diagram for one example of a method 400 for testing one or more test sequences for the existence of malicious signature snippets.

Method 400 begins at step 410.

At step 420, it is determined if the malicious signature snippet is present in at least one test sequence. In some embodiments, the at least one test sequence is a sequence provided for purposes of replication. The sequence may represent a single genetic sequence, or may include regions intended to be "clipped and stitched" later using a mechanism such as CRISPR. In some embodiments, the at least one test sequence may be a full genetic sequence (e.g., representing a full strand of DNA). In other embodiments, the at least one test sequence may be a subsequences of the full genetic sequence. An optimal length of the subsequence, or portion of the full genetic sequence included in the subsequence, may be selected. For example, a test sequence may be a subsequence of a full genetic sequence, the subsequence selected from a location or region of the full genetic sequence based on a likelihood of finding a malicious signature snippet in that region. In still other embodiments, a subsequence may be selected to omit known benign regions of a full genetic sequence.

Malicious signature snippets may be compared to the at least one test sequence at each sequential position on the at least one test sequence. For example, a 3-gram malicious signature snippet may first be compared to positions 1-3 on the at least one test sequence, then to positions 2-4 on the at least one test sequence, etc.

In some embodiments, the number and type of matches may be stored for each at least one test sequence and/or malicious signature snippet. For example, data may be stored indicating the location of each malicious signature snippet on the at least one test sequence, the type of the malicious signature snippet, a number of times each malicious signature snippet occurs in the at least one test sequence, and other information.

Metadata about the malicious signature snippets and/or the corresponding malicious organisms may be used to identify or categorize the test sequence. For example, where multiple malicious signature snippets are found in the test sequence, common characteristics of the matching malicious signature snippets may be determined from the metadata. It may be determined, for example, that the matching malicious signature snippets are all from a particular sample (or related samples) of a specific organism, which may suggest that the customer is trying to replicate that organism. Depending on the number of signature snippets in the test sequence, it may be possible to identify a genus, species, or even particular sample of malicious organism that is reflected in the test sequence.

The type and number of signature snippets corresponding to a malicious organism or organism type may be tracked and analyzed to draw conclusions about the test sequence. For example, if the number, cumulative length, or other statistic of influenza signature snippets in a test sequence exceeds a given threshold, a conclusion may be automatically made that the test sequence is an attempt to synthesize influenza. In another embodiment, such statistics may be used to determine a level of confidence in the determination that the sequence was submitted for nefarious purposes.

At optional step 430, a determination may be made about the at least one test sequence. For example, depending on the number and type of malicious signature snippets occurring on the at least one test sequence, and the malicious organisms to which they relate, a determination may be made to reject the at least one test sequence from a synthesizing/replicating application, and/or to flag the at least one test sequence for further review by the system and/or a user. In some embodiments, a threshold number of occurrences of malicious signature snippets may be set, and a determination made about the at least one test sequence based on whether the threshold is exceeded. Different thresholds may be set for different malicious organisms, with more dangerous pathogens having a low/zero threshold, and less dangerous pathogens having a higher threshold.

Method 400 ends at step 440.

In addition to approaches described above for identifying the presence of malicious organism sequences, there are also applications where it would be useful to quickly categorize test sequences as one or more of a number of organisms (including, but not limited to, pathogens).

Figure 5:
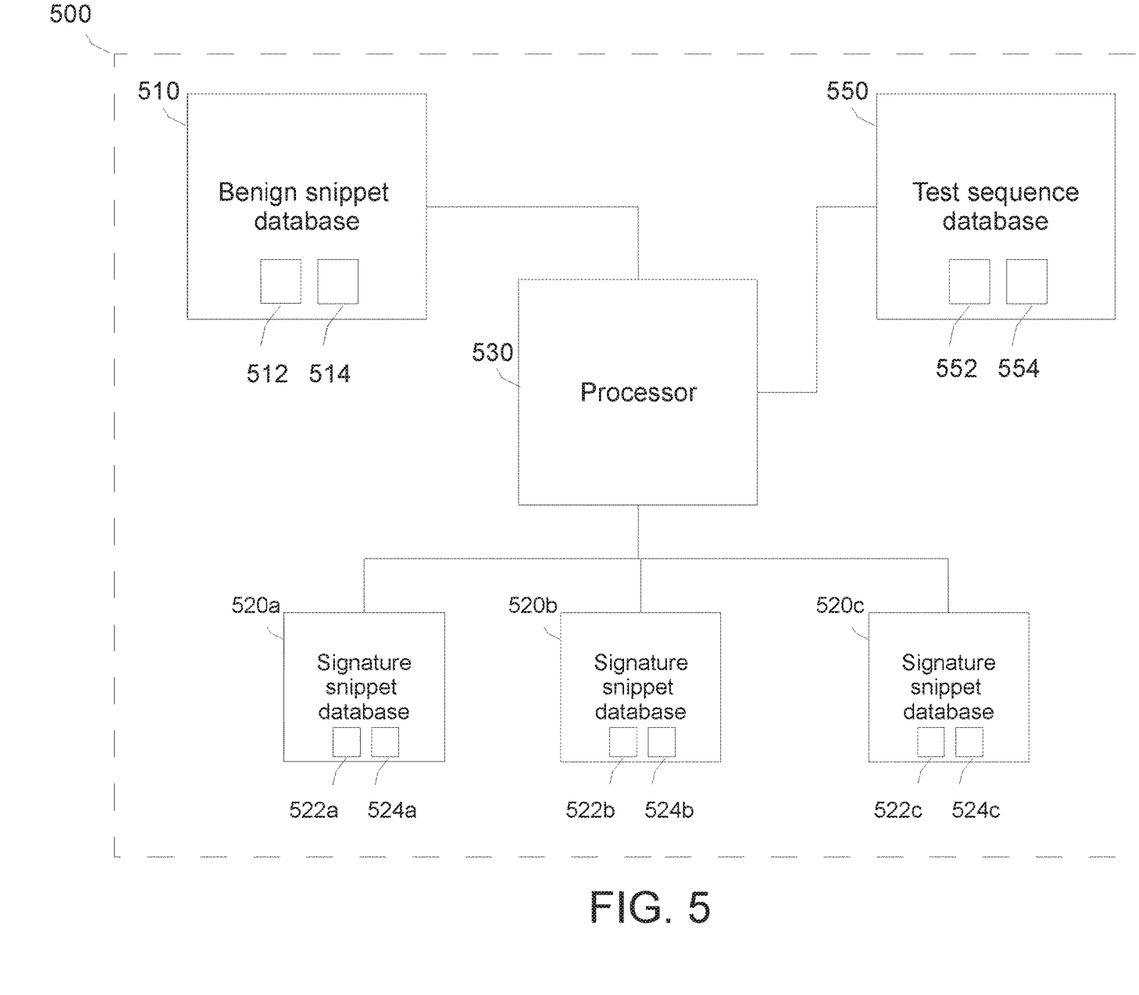
FIG. 5 is a block diagram of another computer system for identifying signature snippets and comparing them to test sequences according to aspects of the invention.

FIG. 5 is a block diagram for a system 500 configured to perform methods of identifying signature snippets that can be used to categorize unknown sequences. System 500 may be similar to system 100 in some aspects, with some differences discussed here.

The system 500 includes at least one benign snippet database 510 configured to store a number of benign snippets 512, 514 derived from benign organism sequences (not shown). The system 500 further includes a plurality of malicious signature databases 520a-c configured to store a number of candidate signature snippets 522a-c, 524a-c derived from malicious organism sequences (not shown). In this approach, each of the malicious signature databases 520a-c may also be organized as a probabilistic data structure, such as Bloom filter. Each of the malicious signature databases 520a-c may correspond to a different malicious organism type or group. For example, malicious signature database 520a may store signature snippets for influenza organisms; malicious signature database 520b may store signature snippets for anthrax organisms; and malicious signature database 520c may store signature snippets for the smallpox virus. Each malicious signature database may also store metadata (not shown) about the snippets stored therein, as described above with respect to malicious signature database 140.

The system 500 further includes a processor 530, configured to compare candidate signature snippets (not shown) to the plurality of benign snippet sequences 512, 514. If no match is found, it may be determined that a particular candidate signature snippet is a suitable signature snippet for a particular type of malicious organism associated with one of the malicious signature snippet databases 520a-c. If so, the candidate signature snippet may be stored in one of the malicious signature snippet databases (e.g., 520b) corresponding to the type of malicious organism. To continue the previous example, if a candidate signature snippet is found to be a suitable signature snippet for influenza, then the candidate signature snippet may be stored as a signature snippet 522a in malicious signature snippet database 520a.

As in system 100, candidate signature snippets in system 500 are extracted from a sequence of a known organism. While the examples discussed here involve malicious organisms, it will be appreciated that the same techniques may be used to identify or categorize non-malicious organisms of interest, as well. The candidate signature snippets may be stored in one or more candidate signature snippet databases (not shown).

Where candidate signature snippets are stored for a number of malicious organisms or malicious organism types, the candidate signature snippets may be stored in one or more databases in any number of manners that allows the candidate signature snippet to be associated with a particular organism or organism type. In one embodiment, candidate signature snippets may be stored in a single candidate signature snippet database, with each candidate signature snippet associated (by an identifier or other association) with a particular malicious organism or malicious organism type. In other embodiments, candidate signature snippets may be stored in different databases according to their associated malicious organism or organism type.

Benign snippets may similarly be stored in a common database, or may be stored separately according to the type of benign organism from which they originate, or according to the malicious organism or organism type for which they are used to identify signature snippets.

As in system 100, system 500 further includes a test sequence database 550 configured to store a number of test sequences 552, 554. During a testing operation of the system 500, one or more of the test sequences 552, 554 in the test sequence database 550 is compared to the signature snippets in one or more of malicious signature snippet databases 520a-c to determine if any of the malicious signature snippets 522a-c, 524a-c are present in the one or more of the test sequences 552, 554. For example, the test sequences 552, 554 may be applied to a Bloom filter of each of the malicious signature snippet databases 520a-c to determine if any matches are found. If so, any of the test sequences 552, 554 matching any of the malicious signature snippets 522a-c, 524a-c may be flagged as containing a sequence (or snippet thereof) of the malicious organism associated with the malicious signature snippet database 520a-c containing such malicious signature snippets.

In some embodiments, the one or more test sequences 552, 554 may be full genetic sequences (e.g., representing full strands of DNA). In other embodiments, the one or more test sequences 552, 554 may be subsequences of a given length, with an optimal length for testing being selected. In some embodiments, the one or more test sequences 552, 554 may first be compared to the malicious signature snippets 522a-c, 524a-c at locations on the one or more test sequences 552, 554 where malicious signatures may be expected to be found. If no matches are found, less likely locations may be examined.

Figure 6:
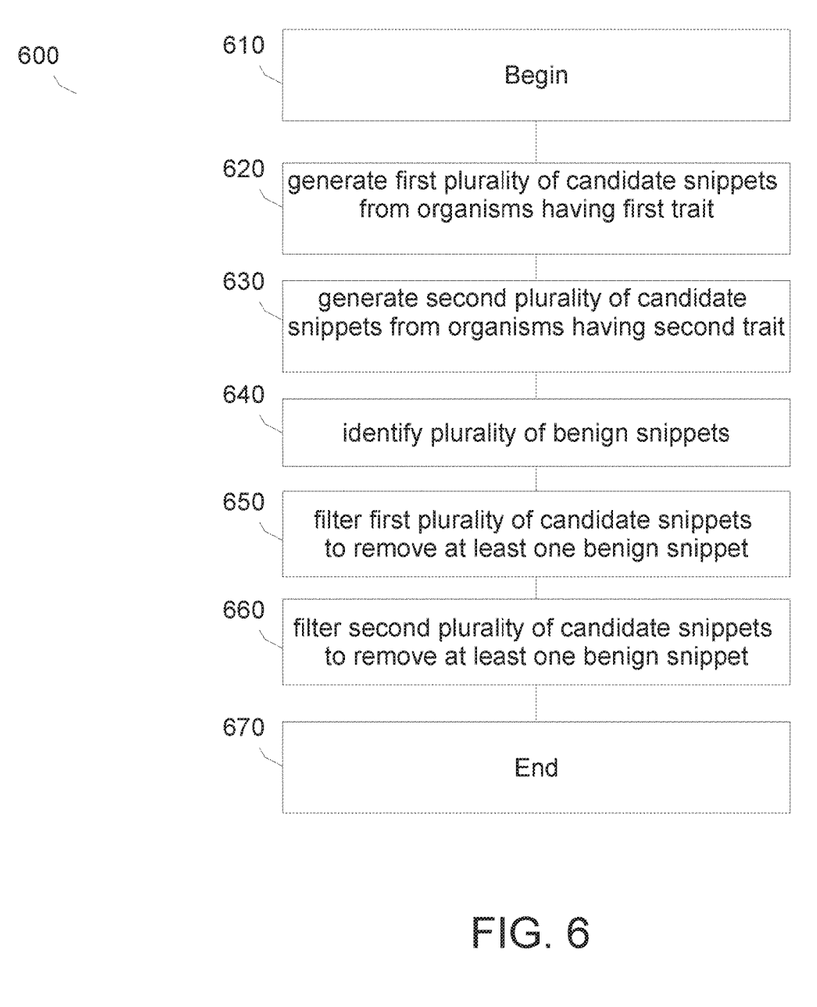
FIG. 6 is a flow diagram of one example of a process of identifying signature snippets according to aspects of the invention.

FIG. 6 is a flow diagram for one example of a method 600 for classifying regions of genetic sequences, such as with system 500.

Method 600 begins at step 610.

At step 620, a first plurality of sequence snippets is generated from a first plurality of organisms having a first trait, and at step 630 a second plurality of sequence snippets is generated from a second plurality of organisms having a second trait. In some embodiments, the extraction is performed as discussed above with reference to FIG. 2B. In particular, In particular, candidate signature snippets of length n may be extracted from sequences obtained from a plurality of malicious organisms having a first trait, and from a plurality of malicious organisms having a second trait. The trait may be a classification or category of the type of organism (e.g., influenza).

In step 640, a plurality of benign sequence snippets is identified. Step 640 may be performed in much the same way as step 320 of method 300. As discussed above, in some embodiments, extraction of the plurality of benign sequence snippets may not be performed by the system. Rather, benign sequence snippets may be provided to the system, for example, by a third party, with the extraction already performed. For example, a database of benign snippets may be made available. In another example, the benign sequence snippets may have been extracted by the system during previous operations and maintained.

In step 650, the first plurality of candidate sequence snippets is filtered to remove at least one of the plurality of benign sequence snippets, and in step 660, the second plurality of candidate sequence snippets is filtered to remove at least one of the plurality of benign sequence snippets. Other pluralities of candidate sequence snippets may also be filtered, as the method is not limited to two such pluralities. Steps 650 and 660 may be performed in much the same way as step 340 of method 300. In particular, each plurality of candidate signature snippets is compared to the benign snippets (e.g., in a Bloom filter), and any candidate signature snippets matching a benign snippet may be identified as not being a suitable signature snippet. Those signature snippets found to be suitable may be stored in one of the malicious signature snippet databases corresponding to the type of organism uniquely identified by the signature snippet. The malicious signature snippet databases may be organized as a plurality of probabilistic data structures, such as a Bloom filter.

Method 600 ends at step 670.

Once the training process is complete, test sequences may be examined to determine if one or more malicious signature snippets are present; if so, the test sequence may be flagged for further review and/or considered for rejection from a synthesizing/replicating process.

Figure 7:
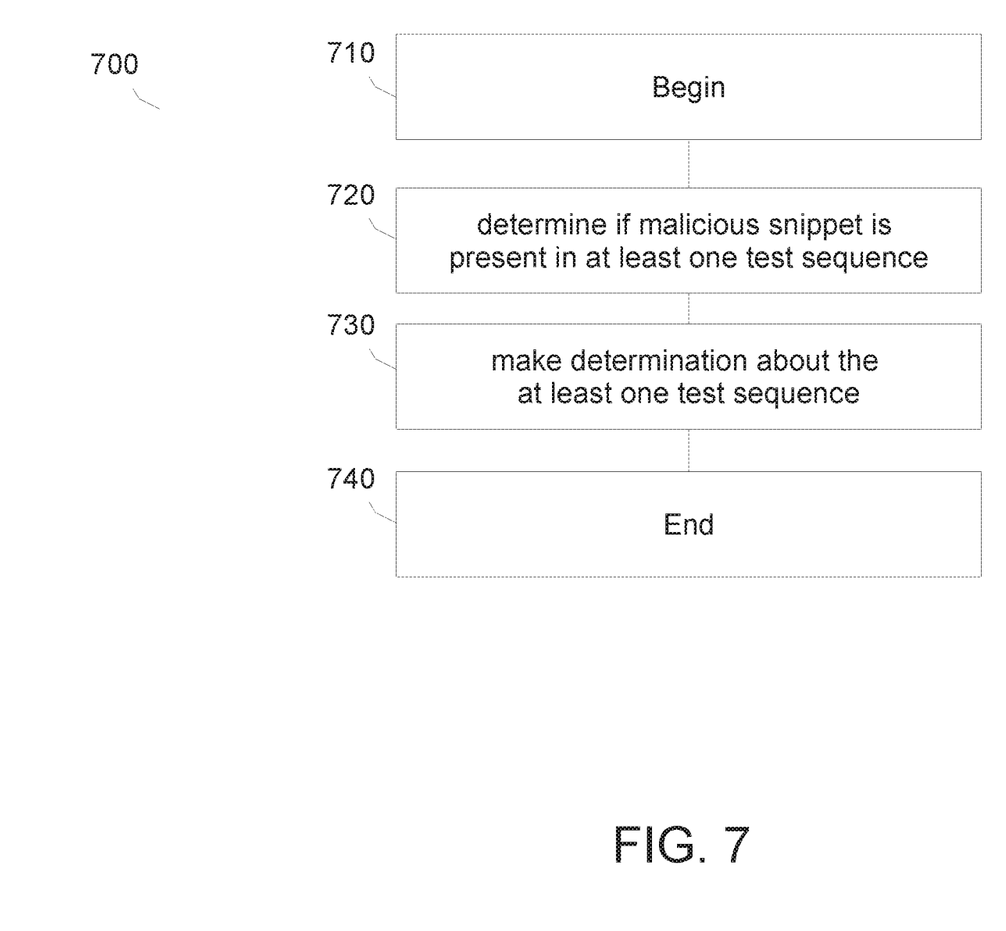
FIG. 7 is a flow diagram of one example of a process of testing test sequences according to aspects of the invention.

FIG. 7 is a flow diagram for one example of a method 700 for testing one or more test sequences for the existence of malicious signature snippets stored in one or more malicious signature databases.

Method 700 begins at step 710.

At step 720, it is determined if the malicious signature snippet is present in at least one test sequence. Step 720 may be performed similarly to step 420 of method 400. The at least one test sequence, or snippets thereof, may be compared to the one or more signature snippets stored (e.g., in Bloom filters) in a plurality of signature snippet databases. In some embodiments, the test sequence may be compared to all of the signature snippet databases, or some standard subset of the signature snippet databases. In other embodiments, particular signature snippet databases may be selected for comparison based on some known characteristic of the test sequence. For example, if it is determined that the test sequence is more likely to contain genetic sequences for influenza, then the test sequence may not be compared to signature snippet databases unrelated to influenza. In some embodiments, the signature snippet databases against which the test sequence is compared may be selectable by a user, e.g., an operator of system 500.

At optional step 730, a determination may be made about the at least one test sequence. Step 730 may be performed similarly to step 430 of method 400.

Method 700 ends at step 740.

Figure 8:
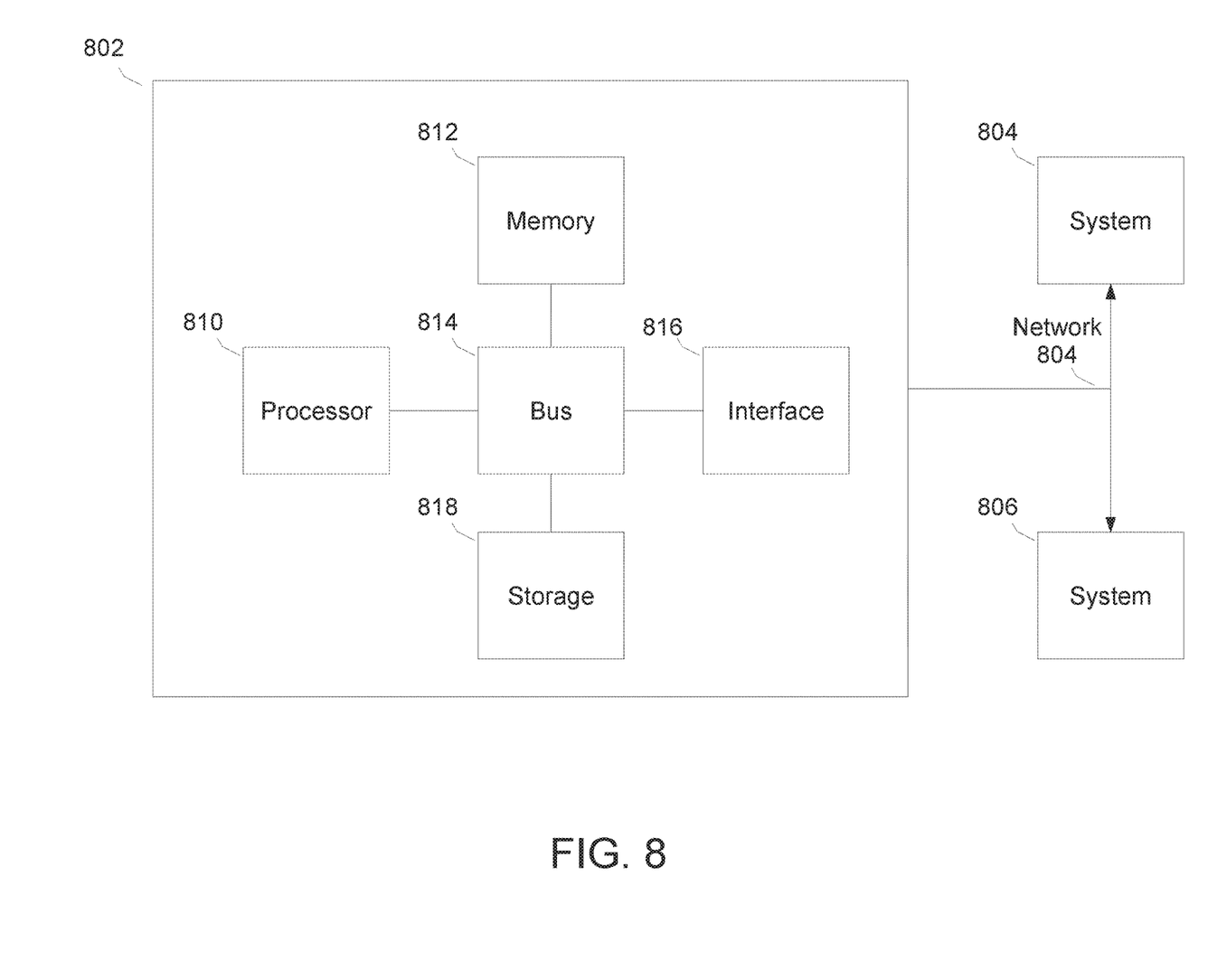
FIG. 8 is a block diagram of one example of a computer system on which aspects and embodiments of the present invention may be implemented.

FIG. 8 is a block diagram of a distributed computer system 800, in which various aspects and functions discussed above may be practiced. The distributed computer system 800 may include one or more computer systems. For example, as illustrated, the distributed computer system 800 includes three computer systems 802, 804 and 806. As shown, the computer systems 802, 804 and 806 are interconnected by, and may exchange data through, a communication network 808. The network 808 may include any communication network through which computer systems may exchange data. To exchange data via the network 808, the computer systems 802, 804, and 806 and the network 808 may use various methods, protocols and standards including, among others, token ring, Ethernet, Wireless Ethernet, Bluetooth, radio signaling, infra-red signaling, TCP/IP, UDP, HTTP, FTP, SNMP, SMS, MMS, SS7, JSON, XML, REST, SOAP, CORBA HOP, RMI, DCOM and Web Services.

According to some embodiments, the functions and operations discussed for producing a three-dimensional synthetic viewpoint can be executed on computer systems 802, 804 and 806 individually and/or in combination. For example, the computer systems 802, 804, and 806 support, for example, participation in a collaborative network. In one alternative, a single computer system (e.g., 802) can generate the three-dimensional synthetic viewpoint. The computer systems 802, 804 and 806 may include personal computing devices such as cellular telephones, smart phones, tablets, "fablets," etc., and may also include desktop computers, laptop computers, etc.

Various aspects and functions in accord with embodiments discussed herein may be implemented as specialized hardware or software executing in one or more computer systems including the computer system 802 shown in FIG. 4. In one embodiment, computer system 802 is a personal computing device specially configured to execute the processes and/or operations discussed above. As depicted, the computer system 802 includes at least one processor 810 (e.g., a single core or a multi-core processor), a memory 812, a bus 814, input/output interfaces (e.g., 816) and storage 818. The processor 810, which may include one or more microprocessors or other types of controllers, can perform a series of instructions that manipulate data. As shown, the processor 810 is connected to other system components, including a memory 812, by an interconnection element (e.g., the bus 814).

The memory 812 and/or storage 818 may be used for storing programs and data during operation of the computer system 802. For example, the memory 812 may be a relatively high performance, volatile, random access memory such as a dynamic random access memory (DRAM) or static memory (SRAM). In addition, the memory 812 may include any device for storing data, such as a disk drive or other non-volatile storage device, such as flash memory, solid state, or phase-change memory (PCM). In further embodiments, the functions and operations discussed with respect to generating and/or rendering synthetic three-dimensional views can be embodied in an application that is executed on the computer system 802 from the memory 812 and/or the storage 818. For example, the application can be made available through an "app store" for download and/or purchase. Once installed or made available for execution, computer system 802 can be specially configured to execute the functions associated with producing synthetic three-dimensional views.

Computer system 802 also includes one or more interfaces 816 such as input devices (e.g., camera for capturing images), output devices and combination input/output devices. The interfaces 816 may receive input, provide output, or both. The storage 818 may include a computer-readable and computer-writeable nonvolatile storage medium in which instructions are stored that define a program to be executed by the processor. The storage system 818 also may include information that is recorded, on or in, the medium, and this information may be processed by the application. A medium that can be used with various embodiments may include, for example, optical disk, magnetic disk or flash memory, SSD, among others. Further, aspects and embodiments are not to a particular memory system or storage system.

In some embodiments, the computer system 802 may include an operating system that manages at least a portion of the hardware components (e.g., input/output devices, touch screens, cameras, etc.) included in computer system 802. One or more processors or controllers, such as processor 810, may execute an operating system which may be, among others, a Windows-based operating system (e.g., Windows NT, ME, XP, Vista, 7, 8, or RT) available from the Microsoft Corporation, an operating system available from Apple Computer (e.g., MAC OS, including System X), one of many Linux-based operating system distributions (for example, the Enterprise Linux operating system available from Red Hat Inc.), a Solaris operating system available from Oracle Corporation, or a UNIX operating systems available from various sources. Many other operating systems may be used, including operating systems designed for personal computing devices (e.g., iOS, Android, etc.) and embodiments are not limited to any particular operating system.

The processor and operating system together define a computing platform on which applications (e.g., "apps" available from an "app store") may be executed. Additionally, various functions for generating and manipulating images may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed components, or any combination thereof. Various embodiments may be implemented in part as MATLAB functions, scripts, and/or batch jobs. Thus, the invention is not limited to a specific programming language and any suitable programming language could also be used.

Although the computer system 802 is shown by way of example as one type of computer system upon which various functions for producing three-dimensional synthetic views may be practiced, aspects and embodiments are not limited to being implemented on the computer system, shown in FIG. 4. Various aspects and functions may be practiced on one or more computers or similar devices having different architectures or components than that shown in FIG. 4.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A computer system comprising:
   one or more processors;
   one or more databases configured to store (a) a first data set comprising a plurality of comparison snippets derived from a plurality of nucleic acid sequences of one or more comparison types, and (b) a second data set comprising a plurality of candidate signature snippets derived from a nucleic acid sequence of a particular type; and one or more computer-readable media storing instructions that, when executed by the one or more processors, cause performance of operations comprising:

performing a computational comparison to determine whether a first candidate signature snippet in the plurality of candidate signature snippets identically matches any comparison snippet in the plurality of comparison snippets in the first data set;

determining, based on the computational comparison, that the first candidate signature snippet does not identically match any comparison snippet in the plurality of comparison snippets in the first data set; and responsive to determining that the first candidate signature snippet does not identically match any comparison snippet in the plurality of comparison snippets in the first data set, identifying the first candidate signature snippet as a first signature snippet that, if found in a given nucleic acid sequence, indicates that the given nucleic acid sequence is of the particular type.

2. The computer system of claim 1, the operations further comprising determining if the first signature snippet is present in at least one test nucleic acid sequence.

3. The computer system of claim 2, the operations further comprising determining, for the first signature snippet and a second signature snippet that both are present in the at least one test nucleic acid sequence, a common characteristic of the first signature snippet and the second signature snippet.

4. The computer system of claim 3, wherein determining the common characteristic is performed with reference to metadata about at least one snippet of the first signature snippet or the second signature snippet.

5. The computer system of claim 4, wherein the metadata includes at least one of an identifier of a genus of an organism from which the at least one snippet was obtained, an identifier of a species of an organism from which the at least one snippet was obtained, and a location at which the at least one snippet was obtained on the nucleic acid sequence of the particular type.

6. The computer system of claim 1, wherein the plurality of comparison snippets and the first candidate signature snippet are one of DNA snippets, RNA snippets, and amino acid snippets.

7. The computer system of claim 1, wherein the first data set comprising the plurality of comparison snippets is arranged in a probabilistic data structure.

8. The computer system of claim 7, wherein the probabilistic data structure is one of a Bloom filter and a search tree.

9. The computer system of claim 1, wherein the plurality of nucleic acid sequences of the one or more comparison types comprises a nucleic acid sequence of a non-malicious strain of an organism having at least one malicious strain.

10. The computer system of claim 1, wherein the plurality of nucleic acid sequences of the one or more comparison types comprises a nucleic acid sequence of an organism that belongs to a genus having at least one malicious organism.

11. The computer system of claim 1, the operations further comprising predicting a minimum number of snippets to be included in the plurality of comparison snippets, the minimum number being sufficient to yield a false positive rate below a threshold, wherein the false positive rate is a rate at which candidate signature snippets identified as signature snippets for nucleic acid sequences of the particular type are present in a nucleic acid sequence of the one or more comparison types.

12. The computer system of claim 11, wherein the minimum number of snippets is selected with reference to an organism of the particular type.

13. The computer system of claim 1, wherein the plurality of comparison snippets is a plurality of n-length subsequences of the plurality of nucleic acid sequences of the one or more comparison types, and wherein the first signature snippet is an n-length subsequence not in the plurality of n-length subsequences.

14. The computer system of claim 1, wherein the plurality of candidate signature snippets includes a first plurality of n-length subsequences of the nucleic acid sequence of the particular type, the first plurality of n-length subsequences each beginning at different positions of the nucleic acid sequence of the particular type, and wherein the plurality of comparison snippets includes a second plurality of n-length subsequences of a known nucleic acid sequence of the one or more comparison types, the second plurality of n-length subsequences each beginning at different positions of the known nucleic acid sequence.

15. The computer system of claim 1, wherein the first signature snippet is a genetic sequence of a pathogen.

16. The computer system of claim 1, wherein the particular type is a category of organisms considered malicious and the one or more comparison types is a category of organisms considered benign.

17. The computer system of claim 1, the operations further comprising:

determining that a second candidate signature snippet in the plurality of candidate signature snippets identically matches a comparison snippet in the plurality of comparison snippets in the first data set; and responsive to determining that the second candidate signature snippet in the plurality of candidate signature snippets in the second data set identically matches the comparison snippet in the plurality of comparison snippets in the first data set, identifying the second candidate snippet as not a suitable signature snippet for the particular type.

18. The computer system of claim 1, the operations further comprising:

after identifying the first signature snippet, storing the first signature snippet in a signature database along with metadata associated with one or more of (a) the first signature snippet and/or (b) the particular type.

19. The computer system of claim 1, wherein the given nucleic acid sequence comprises fewer than two hundred base pairs.

20. One or more non-transitory computer-readable media storing instructions configured so that, when executed by one or more hardware processors, the instructions cause performance of operations comprising:

obtaining a first data set comprising a plurality of comparison snippets derived from a plurality of nucleic acid sequences of one or more comparison types;

obtaining a second data set comprising a plurality of candidate signature snippets derived from a nucleic acid sequence of a particular type;

performing a computational comparison to determine whether a first candidate signature snippet in the plurality of candidate signature snippets identically matches any comparison snippet in the plurality of comparison snippets in the first data set;

determining, based on the computational comparison, that the first candidate signature snippet does not identically match any comparison snippet in the plurality of comparison snippets in the first data set; and responsive to determining that the first candidate signature snippet does not identically match any comparison snippet in the plurality of comparison snippets in the first data set, identifying the first candidate signature snippet as a first signature snippet that, if found in a given nucleic acid sequence, indicates that the given nucleic acid sequence is of the particular type.

21. The one or more non-transitory computer-readable media of claim 20, wherein the particular type is a category of organisms considered malicious and the one or more comparison types is a category of organisms considered benign.

22. The one or more non-transitory computer-readable media of claim 20, the operations further comprising:

determining that a second candidate signature snippet in the plurality of candidate signature snippets identically matches a comparison snippet in the plurality of comparison snippets in the first data set; and responsive to determining that the second candidate signature snippet in the plurality of candidate signature snippets in the second data set identically matches the comparison snippet in the plurality of comparison snippets in the first data set, identifying the second candidate snippet as not a suitable signature snippet for the particular type.

23. The one or more non-transitory computer-readable media of claim 20, operations further comprising:

after identifying the first signature snippet, storing the first signature snippet in a signature database along with metadata associated with one or more of (a) the first signature snippet and/or (b) the particular type.

* * * * *